(12) United States Patent
Watson

(10) Patent No.: US 6,896,681 B1
(45) Date of Patent: May 24, 2005

(54) FINGERTIP DEVICE FOR RUPTURING AMNIOTIC MEMBRANES

(76) Inventor: Richard L. Watson, 1955 Cougar Trail, McPherson, KS (US) 67460

( * ) Notice: Subject to any disclaimer, the term of this patent is extended or adjusted under 35 U.S.C. 154(b) by 407 days.

(21) Appl. No.: 09/758,381

(22) Filed: Jan. 10, 2001

Related U.S. Application Data

(60) Provisional application No. 60/175,357, filed on Jan. 10, 2000.

(51) Int. Cl.⁷ ............................................. A61B 17/42
(52) U.S. Cl. ....................................................... 606/125
(58) Field of Search ................................. 606/125, 119, 606/185, 167–171, 184; 604/176, 115, 22

(56) References Cited

U.S. PATENT DOCUMENTS

| | | | | |
|---|---|---|---|---|
| 2,084,692 A | * | 6/1937 | Little | 128/361 |
| 2,811,969 A | * | 11/1957 | Shubert | 128/303 |
| 2,847,012 A | * | 8/1958 | Eastman | 128/303 |
| 3,362,408 A | * | 1/1968 | Stocki et al. | 128/314 |
| 3,410,269 A | * | 11/1968 | Hovick | 128/361 |
| 3,533,411 A | * | 10/1970 | McKnight | 128/361 |
| 3,587,591 A | * | 6/1971 | Satterwhite | 128/361 |
| 3,624,747 A | * | 11/1971 | McKnight | 128/361 |
| 3,687,139 A |  | 8/1972 | Poirier | 128/361 |
| 3,735,760 A | * | 5/1973 | Vreeland, Jr. | 128/216 |
| 3,741,211 A | * | 6/1973 | Vreeland, Jr. | 128/221 |
| 3,749,099 A | * | 7/1973 | Cotey | 128/361 |
| 4,198,985 A | * | 4/1980 | Abel | 128/361 |
| 4,357,945 A | * | 11/1982 | Janko | 128/771 |
| 4,807,625 A |  | 2/1989 | Singleton | 128/361 |
| 4,892,520 A | * | 1/1990 | Gilbaugh | 604/117 |
| 4,991,592 A | * | 2/1991 | Christ | 600/567 |
| 5,014,717 A | * | 5/1991 | Lohrmann | 600/567 |
| 5,036,589 A |  | 8/1991 | Heinrich | 30/298 |
| 5,087,262 A | * | 2/1992 | Sheahon | 606/125 |
| 5,284,141 A |  | 2/1994 | Eibling | 128/642 |
| 5,846,250 A |  | 12/1998 | Parker, III | 606/125 |
| 5,968,055 A | * | 10/1999 | Dimitriu | 606/125 |
| 6,027,511 A |  | 2/2000 | Shirley et al. | 606/125 |
| 6,409,734 B1 | * | 6/2002 | Zapata | 606/125 |
| 2002/0007186 A1 | * | 1/2002 | Zapata | 606/125 |

OTHER PUBLICATIONS

AmniHook Amniotic Membrane Perforator, Hollister web site, http://www.hollister.com/us/products/product_series.asp?group=4&family=23, printout dated Jun. 24, 2003, publication date unknown.

Obstetrics Illustrated, Kevin P. Hanretty, Churchill Livingstone, May 2003, p. 254.

\* cited by examiner

*Primary Examiner*—John J. Calvert
*Assistant Examiner*—Alissa L. Hoey
(74) *Attorney, Agent, or Firm*—Loeffler Jonas & Tuggey LLP

(57) ABSTRACT

Amniotic sac-rupturing devices are disclosed in various configurations that are mounted on the hand of a physician to present a shielded hook, positioned on the physician's fingertip, supported by a flexible but firm substrate that extends from the fingertip to the palm and yet conforms to the corresponding contours of the finger during use, while still exposing critical portions of the fingertip for digitally examining an expectant mother's cervix prior to rupturing the amniotic sac. The sac-rupturing devices include a split ring mid-length, and a widened base handle that fits in the palm, to also help secure the hook on the physician's finger and ensure that the hook is readily withdrawn from the birth canal after rupturing the amniotic sac. Alternative hook arrangements are also disclosed, as well as methods of using the same.

15 Claims, 4 Drawing Sheets

US 6,896,681 B1

FINGERTIP DEVICE FOR RUPTURING AMNIOTIC MEMBRANES

CROSS REFERENCE TO RELATED APPLICATION

This application claims priority to Provisional Patent Application, Ser. No. 60/175,357, entitled "Fingertip Device For Rupturing Amniotic Membranes", filed Jan. 10, 2000, pursuant to 37 CFR §1.53(c).

BACKGROUND

1. Field of the Invention

The present intention relates to a device for rupturing pregnant mother's amniotic. sac. More particularly, the present invention relates to a safe and easy-to-use sac-rupturing device adapted to be securely positioned on the face of the fingertip of the physician attending to the mother and child, as well as related methods for rupturing the amniotic sac.

2. Background Art

Before birth, every unborn child is securely protected within a thin membrane or sac that lines the inner wall of the womb. The sac, known as the amniotic sac, contains the child as well as a suspension of amniotic fluid that further protects the child. In the latter stages of pregnancy, the cervix begins to dilate, exposing a small portion of the sac such that it becomes the prime barrier holding the baby and fluid from exiting the womb through the cervix In obstetric care, it is often desirable to induce or accelerate labor by rupturing the mother's amniotic sac, a process also known as "breaking her water". By rupturing the amniotic sac, the obstetrician allows a significant portion of the amniotic fluid to escape from the sac, which typically stimulates and enhances uterine contractions to accelerate labor.

Traditionally; physicians have used a hooked instrument that looks much like a crochet needle to hook and pierce the amniotic sac. Such instruments are typically long flat, stick-like structures having a sharp hook at the end. The physician inset the instrument in the cervix and tries to hook part of the amniotic sac so that, upon pulling, the hook will rupture the sac. The procedure can be cumbersome and very uncomfortable for the mother, as it is often difficult to hold the instrument in a stable position and maneuver it within the birth canal and womb.

Other problems arise from the fact that the smooth surface of the amniotic sac can be difficult to hook and puncture. Repeated efforts are often required in order to achieve rupture. Other times, the hook may pierce the sac and engage a part of the fetus. Plus, upon withdrawal of the hook from the patient, it may inadvertently hook the cervix or other surrounding tissue.

The prior art has only partially addressed such problems. Particularly, others have attempted to improve amniotic sac-rupturing devices by mounting a protruding point on a finger cot that is placed over the physician's examination glove. The points of such devices, however, can snag vaginal tissue during insertion and removal. Moreover, such finger cots are prone to slipping off the underlying glove when it is removed from the vaginal passage, presenting obvious inconvenience and potential hazards.

OBJECTS OF THE INVENTION

It is a primary object of the present invention to provide an amniotic sac-rupturing device that is effective and easy to use.

One of the objects of the present invention is to provide an amniotic sac-rupturing device that can be readily maneuvered within the birthing canal and womb. It is a related object of the invention to provide enhanced control of the rupturing device during use. An additional object of the invention is to provide a rupturing device that is ergonomically friendly to the physician's hand and flexibly conforms to the bend of the physicians hand as well as the contours of the mother's birth canal in use. Yet another related object of the present invention is to provide an amniotic sac-rupturing device that can be sterilize and used with a single examination glove, without compromising sterility of portions of the device which typically enter the vaginal passage.

Another object of this invention is to provide an amniotic sac-rupturing device that can be easily held by the physician in a secure manner. A related object is to provide an amniotic sac-rupturing device that can be securely held adjacent the physician's finger and which is adapted to ensure that the device remains adjacent the finger when it is withdrawn from the birth canal. It is another object that the device fits on the physician's hand in a way that does not materially interfere with a digital exam of the cervix. Another object is that such a device be adapted so that it may be readily implemented by a physician without significantly interfering with the physician's sense of touch.

Another object of the present invention is to provide an amniotic sac rupturing device that is adapted to help preclude undesirable snagging of anatomical structures. Still another particular object of this invention is to provide an amniotic sac-rupturing device that precludes undesirable snagging of the fetus, cervix and surrounding tie.

The present invention addresses these and other objects by providing an innovative amniotic sac-rupturing device that alleviates many of the problems encountered by the prior art. Such a rupturing device includes a rupturing hook or prong slimly mountable on the physician's finger. Preferably the prong is positioned on the face of the physician's fingertip, in a manner that leaves the end and sides of the fingertip partially exposed, so they can still feel the mother's anatomical structures. By enabling touch sensation, the physician can still feel the cervix and estimate the degree of cervical dilation even while the device is mounted in place. Then, if desired the physician can immediately proceed with rupturing the amniotic sac. By mounting the rupturing prong on the face of the physician's second finger, the prong can engage the sac by flaring the finger and pressing it into the exposed portion of the sac. Then, with a slight flick of the fingertip, the prong pierces the sac. Preferably, the prong is relatively flush or slightly contoured on its outer surface to avoid unintentional snagging of the cervix or other anatomical structures. A mounting ring and a proximal base handle help keep the device securely in position, while contouring of the device provides added stability in use, which allows for better control of the rupturing prong.

Many other objects, features and advantages of the present invention will become apparent to those of ordinary skill in the art from the foregoing and following descriptions, particularly when considered in conjunction with the prior art, the appended claims, and the accompanying drawings, wherein certain embodiments of the present invention are illustrated by way of example.

BRIEF DESCRIPTION OF THE DRAWINGS

FIG. 4A is a partial side elevation view. FIG. 4B is a cross-section as viewed along sectional plane 4B—4B indicated in FIG. 4A.

FIG. 5A is a partial cross-section as viewed along plane 5A—5A indicated in FIG. 3B. FIG. 5B is a cross-section as viewed along sectional plane 5B—5B indicated in FIG. 3B.

Figure 1:
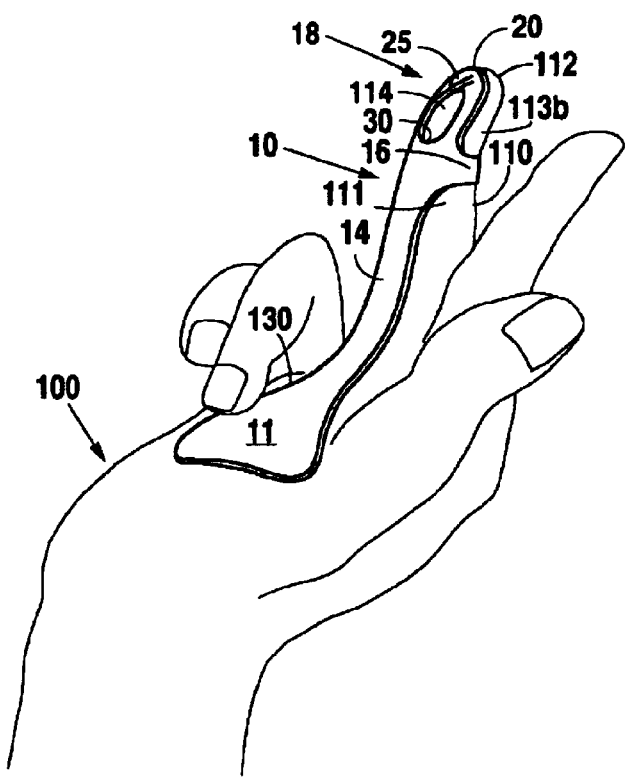
FIG. 1 illustrates a first preferred embodiment of the present invention in the form of an amniotic sac-rupturing device 10; the device 10 is illustrated pictorially in a flexed position as it might be operatively mounted on a physician's hand 100 in use.

It should be understood that the vertical dimensions in FIGS. 4A–5B are exaggerated, for purposes of illustration.

DETAILED DESCRIPTIONS OF PREFERRED EMBODIMENTS

With reference to the accompanying drawings, FIGS. 1–4 illustrate various embodiments of aminiotic sac-rupturing devices that mount on the hand 100 of a physician and are effective and easy to use. Although not part of the present invention, the following descriptions repeatedly reference hand 100 and its various features, as well as various anatomical features of the physician's patient (an expectant mother). Despite the variety of shapes and sizes of such features as they may occur in nature, it may be assumed that such anatomical features are of average-size, shape and orientation Referring to FIGS. 1–2C amniotic sac-rupturing device 10 represents a first preferred embodiment of the present invention. Device 10 bas an elongate structure that is adapted to mount on a finger, preferably the middle finger 110, of a physician's hand 100. As is best observed in FIGS. 2B and 2C, device tom ay be referenced as saving distal end 18 and base handle 11 at its opposite ends, with shank 14 extending between base handle 11 and distal end 18. Ring 16 is formed at the junction between shank 14 and distal end 18. Hook 25 is formed at the tip 20 of distal end 18 for operatively engaging and rupturing an amniotic sac.

Device 10 is preferably formed of an elastically flexible material to allow flexing of shank 14 (and other portions) during use. Although the material known as "Silastic" material is preferred, other flexible materials may also be used within practical limits. To control costs and enable ease of production, device 10 is preferably of uniform composition, although various portions of device 10 may have varied compositions if desired. It may be desired, for instance, to form hook 25 (or, more particularly, edge 27) as a hardened barb that is adjoined to or integrally formed in the distal end 18 of device 10. It may also be desired to reinforce various portions of device 10 for localized strength, such as may be desired in ring 16 and/or in distal end 18.

Figure 2A:
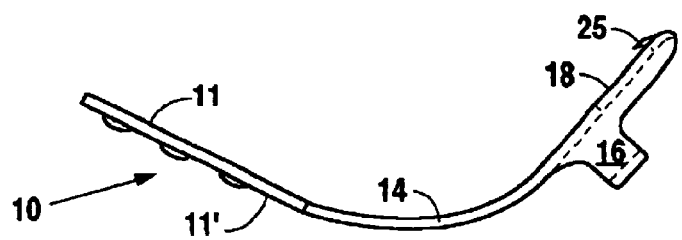
FIG. 2A is a side elevation view of the sac-rupturing device 10 pictorially illustrated in FIG. 1, showing flexure of shank 14 much the same as is illustrated in FIG. 1.

Flexibility of shank 14 allows device 10 to generally conform to the contour of hand 100, particularly finger 110 and palm 130, in use. Referring to FIG. 2A, device 10 is shown un-flexed, in an arcuate shape that tends to conform to the contour of hand 100 in use. The arcuate aspects of such shape are principally limited to shank 14, which is oriented to overly the proximal interphalangeal joint of a physician's hand 100 during typical use. The arcuate and contoured shape of device 10 is preferably provided in the forming process, using techniques well known in the art. Due to its composition and the thin profile of shank 14, shank 14 flexes to conform to the bent contour of hand 100 to enable its passage through the vaginal passage of the mother.

For ease of illustration, FIGS. 2B–3C show shank 14 forced into a flat orientation (i.e., without showing the flexure of FIG. 2A). As may be appreciated by comparing FIG. 2B with FIG. 2C, shank 14 is relatively flat, providing a thin profile (the "profile" of shank 14 being the dimension visible in FIG. 2B) when operatively positioned on hand 100. Distal end 18 is also relatively thin in profiles although the outer edges 18a–18c of distal end 18 are rounded as shown in FIGS. 4A and 4B. (Note that opening 30 is omitted in FIGS. 4A and 4B for purposes of illustration, although device 10 preferably includes such opening 30). The rounded edges 18a–18c provide a contoured shape for distal end 18 to match the typical contour of the face 114 of a physician's finger 110. In use, such contoured shape of distal end 18 provides added stability, which allows for better control of the position and movement of hook 25 relative to finger 110.

Base handle 11 is preferably larger than shank 14 in its width dimension (i.e., the dimension visible in FIG. 2C), which provides a flared proximal end to enable gripping by the hand 100. Such flared aspect of base handle 11 is particularly beneficial while device 10 is being withdrawn from the vaginal passage of a patient. Not only does the flared shape of base handle 11 allow for easy gripping during withdrawal but it also acts to hold itself in place on the palm 130 during such withdrawal. Transverse ridges 12a–12c are preferably added on the surface 11 that faces palm 130, to enhance this self-gripping effect.

Ring 16 is preferably formed integrally with device 10 along its length, and generally serves to help hold device 10 in place on hand 100 during use. Although ring 16 appears to be an unbroken, circumferential ring in the drawings, it is preferably formed as a broken ring to enable its secure placement on fingers of various sizes. Although other positions may be suitable as alternatives, ring 16 is preferably positioned (relative to the other pans of device 10) so that it can be operatively fit on the mid-section 111 of finger 110. Preferably, the size of ring 16 is slightly undersized relative to typical dimensions of midsections 111 of fingers 110 so that, due in part to its elastically flexible composition, ring 16 will tend to securely grip finger 110. Such placement on the midsection 111 of finger 110 allows the tip 112 and sides 113a and 113b of finger 110 to remain exposed to touch, thereby minimizing any interference that device 10 might present in a cervical exam In use, ring 16 cooperates with base handle 11 and the overall shape and composition of device 10 to help keep the device securely in its intended position on hand 100.

Figure 2B:
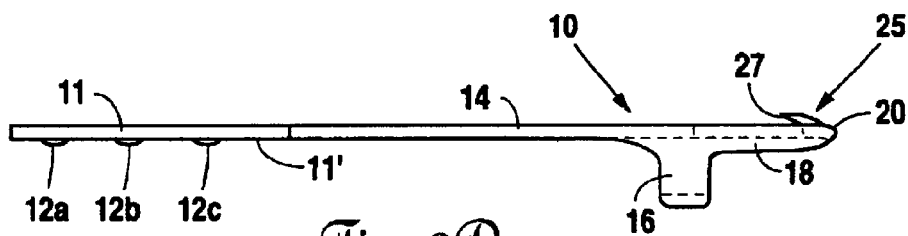
FIG. 2B is a side elevation view of the sac-rupturing device 10 pictorially illustrated in FIG. 1, showing shank 14 forced into a flat orientation for ease of illustration (i.e., without showing the flexure of FIG. 1).
Figure 2C:
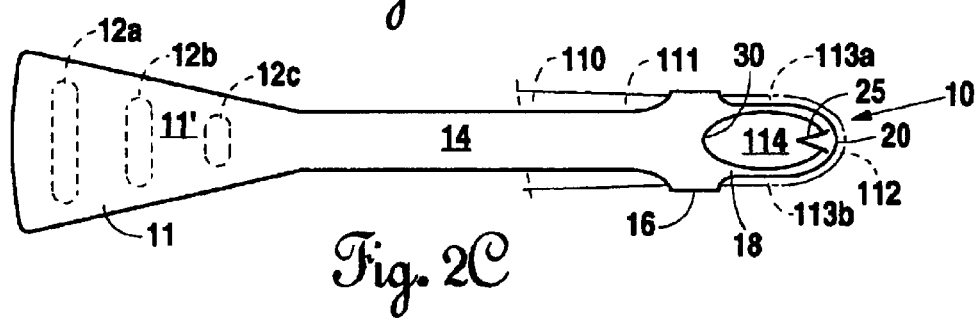
FIG. 2C is an orthogonal top view of the sac-rupturing device 10 of FIG. 2B.

Distal end 18 extends sufficiently beyond ring 16 to position hook 25 over the distal-most portion of the face 114 of the distal segment of finger 110. As shown in FIG. 2C, distal end 18 has a rounded tip that tapers in its width. Hook 25 has a relatively sharp point 25' for operatively engaging and piercing an amniotic sac, although device 10 preferably includes a geometry that tends to shield the point 25' to prevent unintended snagging of anatomical structures. As shown in FIGS. 1 and 2A, hook 25 generally faces base handle 11, away from the tip 20 of distal end 18. Such "rearward" orientation is particularly beneficial to guard against inadvertent snagging while inserting device 10 in the vaginal passage. Further detail of hook 25 can be appreciated from a review of FIGS. 4A and 4B.

FIGS. 4A and 4B are orthogonal views showing further detail of the distal end 18 and hook 25 of amniotic sac-rupturing device 10. Referring to FIG. 4A, the leading surface 26 of hook 25 is preferably smooth and convex in shape (as is tip 20), to ease insertion. Trailing edge 27 (also referred to as cutting edge 27), on the other hand, is a relatively sharp edge that enables cutting of an amniotic sac operatively engaged by hook 25. As visible in FIG. 4A, edge 27 is positioned at an acute angle relative to upper surface 39. Edge 27 generally faces inwardly (i.e., toward opening 30 and the face 114 of finger 110), which provides a concealed cutting edge, concealed or shielded mach like a skinning blade. Although point 25' is sufficiently sharp to puncture an amniotic membrane, edge 27 is sharper than point 25'. Hence, cutting edge 27 is shielded (i.e., shielded from accidentally cutting the wrong tissue) not only by leading edge 26 and the body of hook 25, but also to some degree by point 25'.

As is best shown in FIGS. 1 and 2C, distal end 18 preferably includes a central opening 30 through the profile of distal end 18. Although other shapes may be suitable, opening 30 preferably has an oval shape, elongated along the central longitudinal axis of device 10. Such shape of opening 30, and its placement relative to tip 20 (and other features of device 10), allows it to correspond generally to the oval face 114 of finger 110 in use. Due to the profile thinness of distal end 18, the face 114 of the physician's finger 110 is sufficiently exposed through opening 30 so that the physician can feel anatomical structures through opening 30. Thus, the physician can feel what structures are adjacent distal end 18 in the proximity of opening 30 and, more importantly, in the proximity of the point 25' of hook 25.

Such ability to feel through opening 30 (and opening 60 in the embodiment of FIG. 3) helps prevent inadvertent hooking or snagging of the wrong anatomical structure. Moreover, it also allows the physician to sense what type of sac-rupturing force might be best for rupturing the amniotic sac. For instance, if the physician senses the baby's scalp immediately beyond the amniotic membrane next to point 25', then extra care may be taken to avoid scratching the scalp; whereas, less care may be needed if a sizable pocket of fluid is present.

The resulting structure of amniotic sac-rupturing device 10 is effective and easy to use. Although a variety of dimensions will be suitable, preferably device 10 has an overall length (from the bottom of base handle 11 to the tip of tip 20) of about six or seven inches (when flattened as illustrated in FIG. 2B). The general thickness of the silastic shank 14 (and other portions) is preferably from about one-sixteenth to one-fourth of an inch. The width of shank 14 (i.e., the dimension best visible in FIG. 2C) is preferably about three-eighths of an inch, and the width of distal end 18 is slightly larger, to allow it to conform more to the tip of finger 110. The widest width, at the bottom of base handle 11 is about two-and-a-half inches. Again, such dimensions are submitted just as example and are not to be considered as limiting the invention.

Preparing device 10 for use is simple. When a physician desires to rupture an expectant mother's amniotic sac, (after donning a sterile examination glove (not shown) on hand 100) the physician prepares to secure device 10 to his hand 100 by grasping base handle 11 with the opposite hand. Because base handle 11 does not enter the mother's vaginal passage in use, base handle 11 can be grasped by a non-sterile hand without materially compromising sterility. Grasping handle 11 with the opposite hand, device 10 is then secured to middle finger 110 by pulling 16 onto finger 110 until ring 16 snugly slides onto the midsection 111 of finger 110. As a result, device 10 is secured on hand 100 in an orientation with base handle 11 in the palm 130 and hook 25 near the tip 112 of finger 110.

The physician then inserts device 10 into the mother's vaginal passage together with finger 110. The slim profile and convex leading surface of hook 25 help should point 20' from inadvertent snagging during insertion. Then, before actually rupturing the sac, the physician can digitally examine the cervix with the tip 112 and sides 113 of finger 110. Assuming the physician still desires to rupture the sac after the digital exam, hook 25 is already in position at the tip of the face 114 of finger 110. With a slight fare of finger 110, the sharp point 25' of hook 25 is fully exposed to the amniotic membrane and, with a flick of the finger 110, the sac can be readily ruptured.

It should be understood that the more point 25' of hook 25 is shielded, the more difficult it may be to use it to engage and pierce the amniotic sac. With particular reference to device 40 of FIGS. 3A and 3B, however, alternative embodiments of the present invention may allow even greater shielding of the piercing point than represented in device 10. Device 40 is described further herein as one example which includes such greater shielding of hook 25.

Figure 3A:
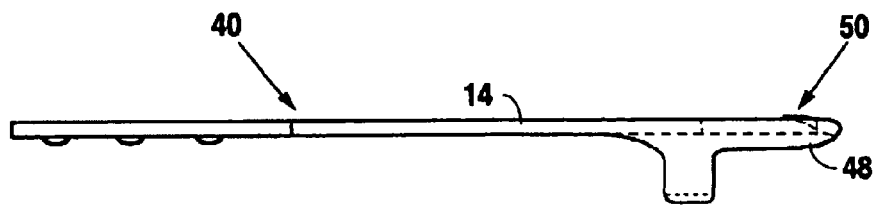
FIGS. 3A and 3B are orthogonal views of a second preferred embodiment of the present invention in the form of an amniotic sac-rupturing device 40, flatly illustrated in much the same perspective as FIGS. 2B and 2C, respectively.
Figure 3B:
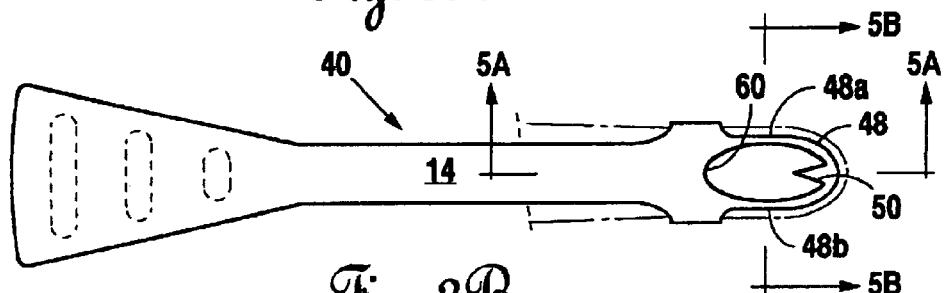
Figure 4A:
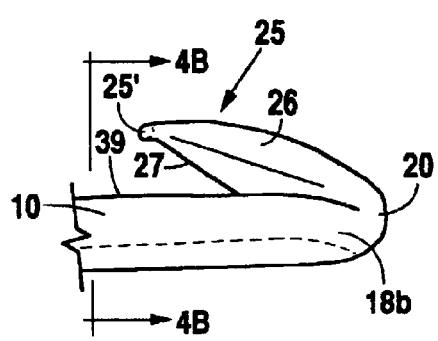
FIGS. 4A and 4B are orthogonal views of the distal end 18 of amniotic sac-rupturing device 10 shown in FIGS. 1–2C.
Figure 4B:
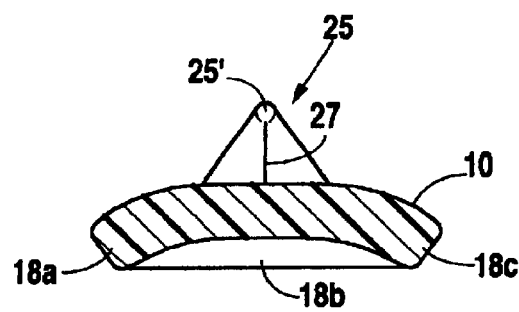
Figure 5A:
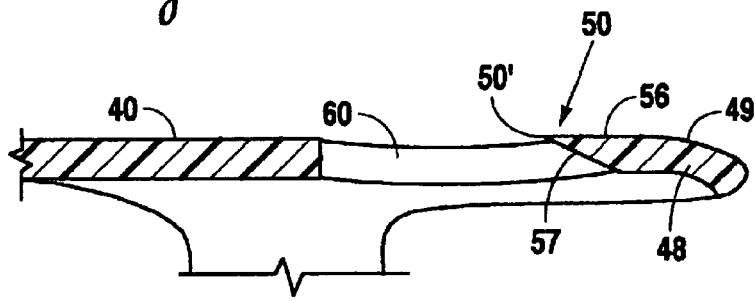
FIGS. 5A and 5B are orthogonal views of the distal end 48 of amniotic sac-rupturing device 40 shown in FIGS. 3A and 3B.
Figure 5B:
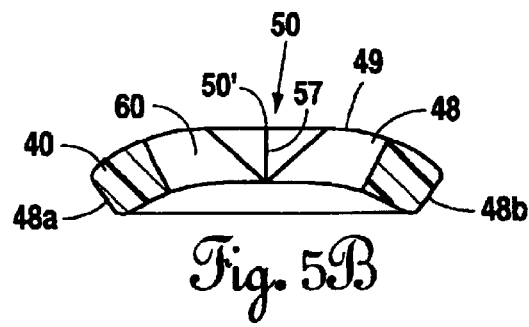

With reference to FIGS. 3A and 3B, amniotic sac-rupturing device 40 represents a second preferred embodiment of amniotic sac-rupturing devices that mount on the hand 100 of a physician and are effective and easy to use. For comparison, device 40 is substantially identical to device 10, except that certain features of distal end 48 and prong 50 of device 40 are slightly different than corresponding features of distal end 18 and hook 25 of device 10. Such differences are described below, although the reader is directed to the description of device 10 for a general description of the similar features FIGS. 5A and 5B are orthogonal views showing detail of prong 50 and related features of distal end 48. As is evident in FIGS. 5A and 5B, distal end 48 includes a central opening 60 through the profile of distal end 48. As with opening 30 of device 10, due to the thin profile of distal end 48, the face 114 of finger 110 is exposed through opening 60. Opening 60 also provides an effective recess in the top surface 49 of distal end 48, within which prong 50 is further shielded from inadvertent snagging. Hence, rather than protruding toward the patient, the leading surface 56 of prong 50 is substantially flush with the top surface 49 of distal end 48, which faces the patient in use.

To enable piercing of the amniotic sac, the cutting edge 57 an the underside of prong 50 tapers toward leading surface 56 to provide a sharper point at point 50'. Due to the flexible nature of distal end 48 (particularly, lateral portions 48a and 48b), a physician can readily flex distal end 48 so that point 50' is flared slightly out of opening 60. In the birth canal, such flaring of point 50' increases the exposure of point 50' to the amniotic sac while allowing point 50' to remain flush when not flared, to avoid inadvertent snagging. Moreover, due to opening 60, the physician can better feel whether the sac is the structure being engaged for piercing.

Figure 6:
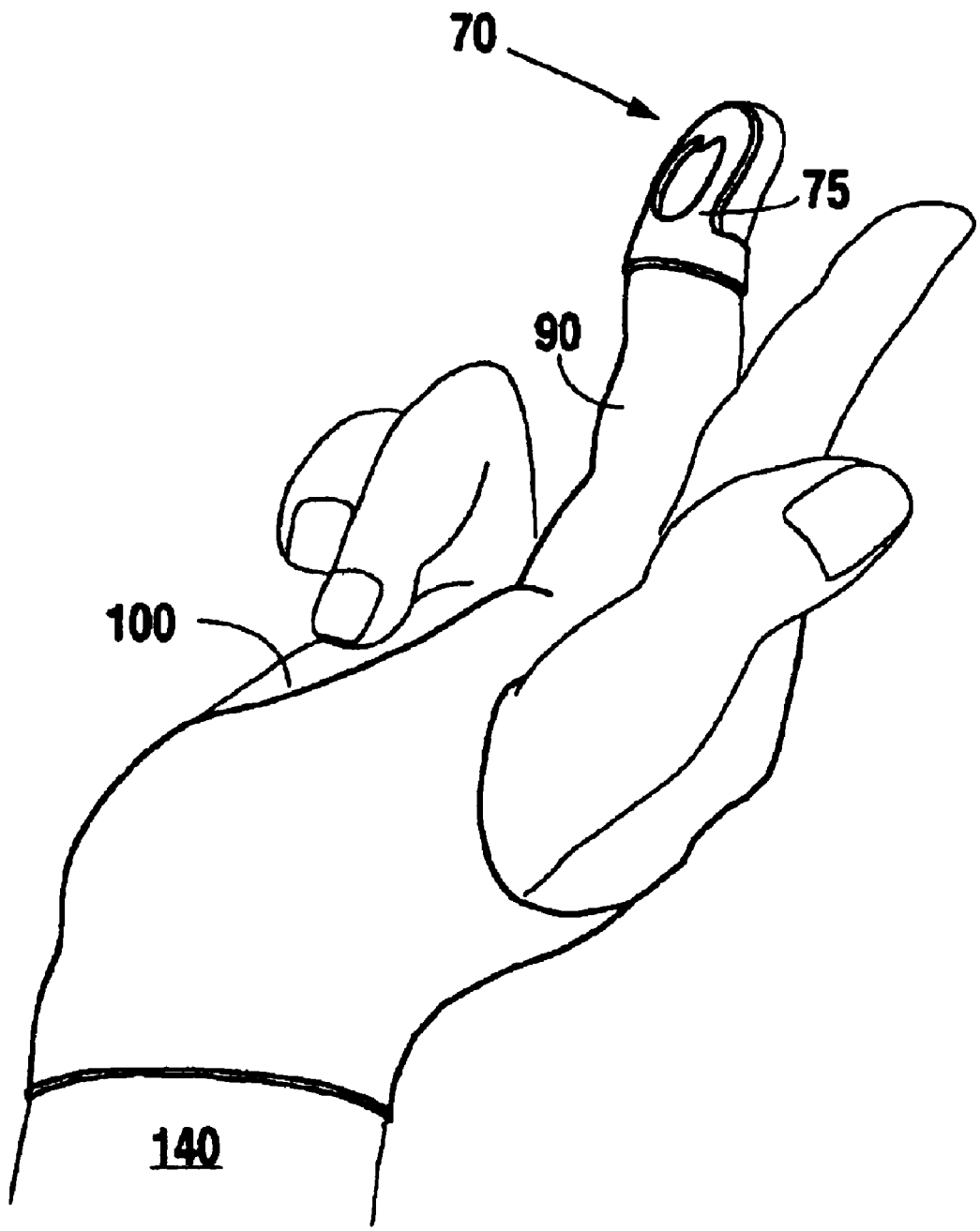
FIG. 6 illustrates a third embodiment of the present invention in the form of an amniotic sac-rupturing device 70, illustrated pictorially mounted in a flexed position on hand 100 much the same as the pictorial illustration of device 10 in FIG. 1.

FIG. 6 illustrates a third embodiment of the present invention in the form of an amniotic sac-rupturing device 70, illustrated pictorially mounted in a flexed position on hand 100 much the sane as the pictorial illustration of device to in FIG. 1. The structure and operation of device 70 will be understood from the description of device 40, with the added understanding that device 70 substitutes a glove-like device 90 in place of the shank and base handle of the other illustrated embodiments. The distal end 75 of device 70 is preferably identical to either distal end 18 or distal end 48 described previously. Distal end 75, however, is adhered or otherwise secured to a glove-like device 90, which holds device 70 in place by snuggly wrapping around wrist 140 of the physician's hand 100. As is evident from FIG. 6, glove-like device 90 is preferably shaped like a glove (or portions of a glove), although it is preferably formed of stronger material than a typical surgical glove. As an alternative, glove-like device 90 may be formed by cutting a surgical glove to be shaped in the depicted manner of FIG. 6, and then reinforcing the remaining portions. Amniotic sac-rupturing device 70 is otherwise used in a manner as above described relative to devices 10 and 40, with similar advantages and results.

Figure 7:
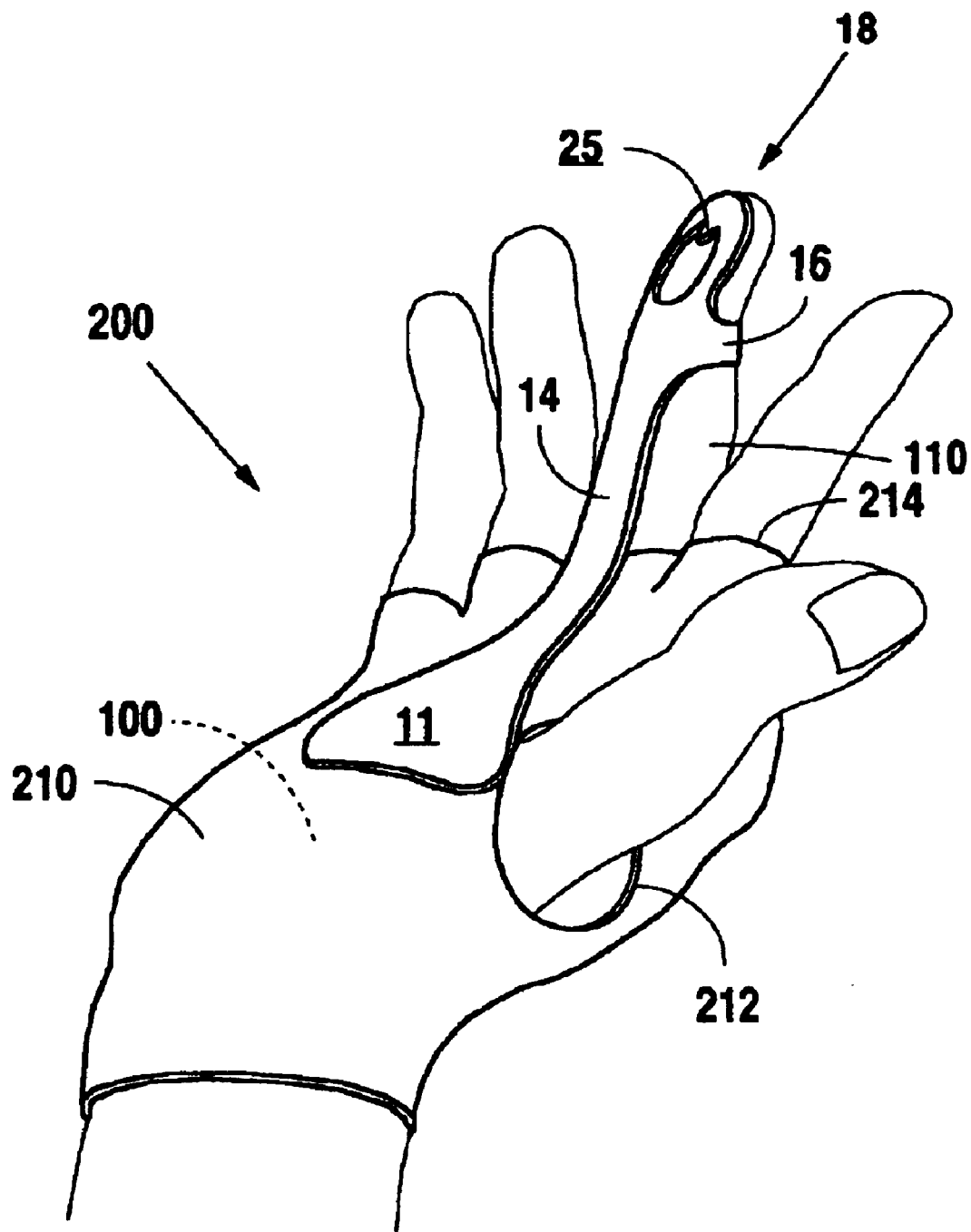
FIG. 7 is a perspective view illustrating a fourth embodiment of the present invention in the form of an amniotic sac-rupturing device 200 mounted on a hand 100.

Many other alternatives, modifications and variations of the foregoing and other embodiments may be utilized while still falling within the scope of the present invention. Many features of the embodiments may be substituted by other, functionally-equivalent features, and many features may be omitted entirely. Some features of one embodiment might also be combined with features of another embodiment. One alternative, for instance, might include an amniotic sac-rupturing device such as device 40 (or parts thereof) while also including something equivalent to aspects of the glove-like device 90, perhaps in the form of shank 14 and distal end 48 adhered or integrally formed with a surgical glove to ensure sufficient strength of the resulting combination. FIG. 7 illustrates an example of such an alternative embodiment 200 having a shank 14 with base handle 11 and distal end 18 and hook 25 like device 10 discussed above wherein the shank 14 is attached to a glove-like device 210 that fits onto a user's hand 100. Like device 10 discussed above, device 200 may have a ring 16 for engaging finger 110 of a user. Glove-like device 210 may have openings 212 and 214 for accommodating the user's thumb and fingers. Other alternatives might include other features that have not been described here. The variations are countless.

Accordingly, the amniotic sac-rupturing devices 10, 40, 70 and 200 enable safe and effective apparatus and methods for rupturing a mother's amniotic sac.

It is to be understood that, while certain embodiments of the present invention have been illustrated and described, such embodiments are examples only. The invention is not to be limited by such descriptions, but rather is defined by the claims appended hereto (as such claims may be amended hereafter) and functional equivalents thereof.

I claim:

1. An amniotic sac-rupturing device adapted to be secured on the hand of a physician for rupturing the amniotic sac of an expectant mother, comprising:

an elongate, flexible shank having a proximal end and a distal end thereof;

a rearward facing sharp point mounted on the distal end of said shank, suitable for puncturing an amniotic sac;

said shank having sufficient length such that said proximal end rests in the palm of the physician's hand while said point is positioned on the face of a fingertip of the physician's same hand;

a ring connected to said shank, said ring being positioned relative to said shank and adapted to secure said shank to a midsection of the physician's finger.

2. The amniotic sac-rupturing device of claim 1, wherein said point is formed at a tip of a hook having a shielded cutting edge.

3. The amniotic sac-rupturing device of claim 2, wherein a leading edge of said hook is substantially flush with a surface of said distal end; and wherein said hook is positioned in a recess in said distal end.

4. The amniotic sac-rupturing device of claim 2, wherein said distal end comprises an upper surface and said cutting edge forms an acute angle relative to said upper surface.

5. The amniotic sac-rupturing device of claim 2, wherein said cutting edge is sharper than said point.

6. The amniotic sac-rupturing device of claim 3, wherein said distal end is sufficiently flexible to permit said point to be flared slightly out of said recess.

7. The amniotic sac-rupturing device of claim 3, wherein said recess comprises an opening through said distal end.

8. The amniotic sac-rupturing device of claim 1, wherein said shank is relatively flat and thin.

9. The amniotic sac-rupturing device of claim 1, wherein said proximal end of said shank comprises a flared base handle.

10. The amniotic sac-rupturing device of claim 9, wherein said base handle comprises at least one ridge engageable on the palm of the physician's hand.

11. The amniotic sac-rupturing device of claim 1, wherein said shank has an arcuate shape in an unflexed state.

12. The amniotic sac-rupturing device of claim 1, further comprising at least a portion of a glove to which said shank is attached.

13. An amniotic sac-rupturing device adapted to be secured on the hand of a physician for rupturing the amniotic sac of an expectant mother, comprising:

an elongate, flexible shank having a proximal end and a distal end;

said proximal end having a flared base handle;

said distal end having an opening therethrough and a rearward facing sharp point suitable for puncturing an amniotic sac;

said point being formed at a tip of a hook having a shielded cutting edge;

said hook being recessed in said opening and having a leading edge that is substantially flush with a surface of said distal end;

said shank being relatively flat and thin and having an arcuate shape in an unflexed condition;

said shank having sufficient length such that said proximal end rests in the palm of the physician's hand while said distal end is positioned on the face of a fingertip of the physician's same hand;

said opening allowing the physician to feel anatomical structures with the face of the fingertip;

said distal end being sufficiently flexible to permit said point to be flared slightly out of said opening;

a ring connected to said shank, said ring being positioned relative to said shank and adapted to secure said shank to a midsection of the physician's finger.

14. The amniotic sac-rupturing device of claim 13, wherein said opening comprises an oval shaped opening.

15. The amniotic sac-rupturing device of claim 13, wherein said base handle comprises at least one ridge engageable on the palm of the physician's hand.

* * * * *